United States Patent [19]

Lin et al.

[11] 4,093,715

[45] June 6, 1978

[54] 5-IODO-5'-AMINO-2',5'-DIDEOXYCYTIDINE AND THE PHARMACEUTICALLY ACCEPTABLE SALTS THEREOF

[75] Inventors: Tai-Shun Lin, North Haven; H. William Prusoff, Branford; David C. Ward, Guilford, all of Conn.

[73] Assignee: Research Corporation, New York, N.Y.

[21] Appl. No.: 792,011

[22] Filed: Apr. 28, 1977

[51] Int. Cl.² .................... A61K 31/70; C07H 19/06
[52] U.S. Cl. .................................... 424/180; 536/23
[58] Field of Search ........................... 424/180; 536/23

[56] References Cited

U.S. PATENT DOCUMENTS

| | | | |
|---|---|---|---|
| 3,687,931 | 8/1972 | Verheyden et al. | 536/23 |
| 3,910,885 | 10/1975 | Moffatt et al. | 536/23 |
| 3,928,319 | 12/1975 | Jenkins et al. | 536/23 |
| 4,000,260 | 12/1976 | Prusoff et al. | 536/23 |

*Primary Examiner*—Johnnie R. Brown
*Attorney, Agent, or Firm*—Cooper, Dunham, Clark, Griffin & Moran

[57] ABSTRACT

The compound 5-iodo-5'-amino-2',5'-dideoxycytidine and the pharmaceutically acceptable acid addition salts thereof are potent inhibitors of herpes simplex virus.

7 Claims, No Drawings

5-IODO-5'-AMINO-2',5'-DIDEOXYCYTIDINE AND THE PHARMACEUTICALLY ACCEPTABLE SALTS THEREOF

The invention described herein was made in the course of work under a grant or award from the Department of Health, Education and Welfare.

BACKGROUND OF THE INVENTION

Herpes simplex viruses are the causative agents in a number of mammalian infections, for example, such human diseases as keratitis, herpes labialis (cold sores), cutaneous herpes, herpes zoster, herpes genitalis, herpes encephalitis, neonatal herpes, herpetic whitlow and acute herpetic gengivostomatitis. Poxviruses, especially poxvirus variolae, are the causative agents of smallpox in man. No completely satisfactory antiviral agent combining high potency and low toxicity has yet been discovered. Accordingly, considerable research effort has been expended in attempts to discover a suitable agent.

THE INVENTION

It has now been discovered that compounds selected from the group consisting of 5-iodo-5'-amino-2',5'-dideoxycytidine and its pharmaceutically acceptable acid addition salts are potent inhibitors of herpes simplex virus, and are substantially non-toxic. For convenience, this compound will hereinafter be referred to as AIC. This invention relates to these novel compounds and to therapeutically useful compositions containing one or more of them, whether or not associated with other therapeutically active ingredients.

The following example illustrates the synthesis of AIC. Pharmaceutically acceptable acid addition salts are readily prepared by treatment of the basic compound with acid in aqueous media followed by evaporation of the solvent, for example, by freeze drying. The salts are generally more soluble than the free base, and are often preferred for the preparation of water based dosage forms such as eye drops. For example, a suspension of free amine in distilled water may be treated with an equivalent amount of aqueous acid, and the resulting solution stabilized with a buffer, such as phosphate buffered saline.

The acids which may be used to prepare the pharmaceutically acceptable acid addition salts of this invention are those containing non-toxic anions and include, for example, hydrochloric, sulfuric, phosphoric, acetic, lactic, citric, tartaric, oxalic, succinic, maleic, gluconic, saccharic and the like.

Melting points are taken on a Thomas-Hoover Unimelt apparatus and are not corrected. A Perkin-Elmer 15 instrument is used to determine the Ir spectra. The UV spectra are taken on a Beckman-25 spectrophotometer. The NMR spectra are recorded on a Bruker 270 HX spectrometer.

EXAMPLE 1

5-Iodo-5'-O-p-tolylsulfonyl-2'-deoxycytidine

To a suspension of 5-iodo-2'deoxycytidine (17.65g, 50.00 mmol) in 250 ml of dry pyridine at 0° (ice bath) is added p-toluenesulfonyl chloride (11.50g, 60.00 mmol). The reaction mixture is stirred at 0° for 1 h and then stored at 3° in the dark with stirring for an additional 23 h. At the end of the reaction a clear solution is obtained, to which 15 ml of methanol is added. After standing for 30 min, the solvent is removed under diminished pressure at room temperature to afford a syrup which is coevaporated several times with methanol. The residue is triturated with icecooled water to give a crystalline mass which is broken down to the fine particles with a spatula. The solid material is collected by filtration, washed thoroughly with water, a small amount of icecooled ethanol, ether, and dried in vacuo to yield 20.24 g (80%) of the desired product.

EXAMPLE 2

5-Iodo-5'-azido-2',5'-dideoxycytidine

A mixture of the compound of Example 1 (2.80 g, 5.52 mmol) and lithium azide (0.41 g, 8.28 mmol) in 30 ml of DMF is heated to 75°-80° (oil bath) for 2 h. The solvent is evaporated to dryness under reduced pressure. The residue is coevaporated several times with ethanol and triturated with ether. The white solid is collected by filtration, washed with ice-cooled water, a small amount of ethanol and ether, and then dried under reduced pressure to afford 1.35 g (65%) of the desired product. An analytical sample is obtained by recrystallization from 95% ethanol; mp 185°-186° (dec); ir (KBr): 4.78 $\lambda$ (azido).

Anal. Calcd for $C_9H_{11}IN_6O_3$: C, 28.59; H, 2.93; N, 22.23; I, 33.56. Found: C, 28.82; H, 3.01; N, 21.96; I, 34.01.

EXAMPLE 3

5-Iodo-5'-amino-2',5'-dideoxycytidine

A mixture of the 5'-azido derivative (7.55 g, 19.97 mmol) and triphenylphosphine (8.38 g, 31.95 mmol) in 250 ml of pyridine is stirred magnetically at room temperature and a clear solution is obtained after 1 h. The reaction mixture is stirred for another 30 min, and after addition of 25 ml of conc $NH_4OH$ solution stirred at room temperature for an additional 3 h. The solvent is evaporated below 30° under reduced pressure to yield a gummy syrup which is coevaporated several times with ethanol, and triturated with ether to form a crystalline mass which is pulverized, and extracted with benzene (5 × 150 ml) and ether (5 × 200 ml). The insoluble solid powder is collected by filtration, washed with more benzene and ether, then dried and extracted with 1 N $NH_4OH$ solution (3 × 150 ml). The insoluble material is removed by filtration and the solution evaporated to dryness in vacuo. The residue is dissolved in boiling ethanol (~150 ml) and filtered through a sintered glass funnel. Ether (1500 ml) is added to the filtrate with stirring, and fine crystals formed. The mixture is maintained at 0° for several hours, during which time more crystals form. The fine pale yellow crystals are collected by filtration, washed thoroughly with ether, and dried under reduced pressure to afford 3.42 g of product. The filtrate and the ether washings are combined and kept at −20° overnight during which time more crystals formed to yield an additional 0.58 g of product. The total yield is 4.10 g (58%); mp 190°-191° (dec); uv: $\lambda_{max}^{0.01\ N\ HCl}$ 299 (nm) ($\epsilon$7,680); $\lambda_{min}^{0.01\ N\ HCl}$ 260 nm; $\lambda_{max}^{0.01\ N\ NaOH}$ 291 nm ($\epsilon$6,270); $\lambda_{min}^{0.01\ N\ NaOH}$ 263 nm; NMR (DMSO-$d_6$): $\delta$2.05 (m, 2, H- 2'), 2.74 (d, 2, H-5'), 3.69 (m, 1, H-4 '), 4.15 (m, 1, H-3'), 5.17 (br. S, 3, C-3' OH, C-5' $NH_2$), 6.06 (t, 1, j = 6.62 Hz, H-1'), 6.63 (br. s, 1, C-4 C = NH), 7.85 (br. s, 1, $N^3$-H), 8.28 (s, 1, H-6).

Anal. Calcd for $C_9H_{13}IN_4O_3$: C, 30.70; H, 3.72; N, 15.91. Found: C, 30.98; H, 3.74; N, 15.52.

EXAMPLE 4

Acid Addition Salts

A total of 177 mg (0.5 mM) of 5-iodo-5'amino-2', 5'dideoxycytidine is suspended in distilled water and 0.55 ml of 1 M HCl added slowly with stirring to provide a solution of the amine hydrochloride salt. The salt is recovered by freeze-drying.

Other acid addition salts, specifically the salts of sulfuric, phosphoric, acetic, lactic, citric and tartaric are similarly prepared.

The products of this inventin may be administered alone, but will generally be administered with pharmaceutically acceptable, non-toxic carriers, the proportions of which are determined by the suitability and chemical nature of the particular carrier, the chosen route of administration, and standard pharmaceutical practice. For example, in combating various infections or in maintaining therapeutically effective levels in blood or tissues, they may be administered orally in the form of tablets or capsules containing such excipients as starch, milk sugar, certain types of clay, etc. They may be enteric coated so as to be more resistant to the acid and digestive enzymes of the stomach. For intravenous and intramuscular administration they may be used in the form of a sterile solution containing other solutes, for example, enough saline or glucose to make the solution isotonic. A wide variety of dosage unit forms are possible.

The physician or veterinarian in attendance will determine the dosage regimen which will be effective. This will depend upon such factors as the age and weight of the patient, the degree and locus of the infection and the dosage unit form selected. Dosage unit forms containing from 25 to 250 mg are useful.

The compounds of this invention manifest a high order to inhibition with various herpes simplex viruses. For example, when tested against strain HSV-1 (prototype) at a concentration of 400 $\mu$M the average log reduction in titre was 1.4. No cytotoxicity is evident even at treatment levels as high as 1600 $\mu$M. Comparable compounds which have been suggested as antiviral agents do not combine this high order of activity with low toxicity. For example, idoxuridine, while it shows a high order of activity at relatively low levels, is almost totally cytotoxic at a concentration of 50 $\mu$M.

Standard procedures were used to maintain the virus and the Vero cells. This included growth and titration by plaque assay as well as the replications of the virus in the presence of the test compounds. Cells were maintained and infected in Dulbecco's medium with 10% fetal calf serum.

For testing, the cells were infected with virus at a ratio of approximately 10 plaque forming units per cell. The viral inoculum was drained after one hour adsorption at 37° C. An appropriate volume of medium containing the compound for testing was added. After 36–48 hours at 37° C, the infected cells were frozen until ready for titration.

Acute toxicity of AIC in mice indicates no lethality at 200 mg/kg of body weight. However, at a level as high as 400 mg/kg the compound is lethal to mice. These figures coupled with the high order of activity indicate a good therapeutic index.

The compounds of this invention are particularly useful for the treatment of herpes simplex keratitis in mammals.

At the present time, the generally accepted therapy for acute herpes simplex keratitis includes the use of 5-iodo-deoxy-uridine (IdUrd). Although the clinical value of this compound has been well established, there is a need for alternative antiviral therapy for ocular herpetic infections. IdUrd-resistant strains of herpes simplex virus Type 1 have been found. Additionally, the compound exhibits significant cellular toxicity. This is manifested in undesirable side effects such as the development of follicular and papillary conjunctivitis, and epithelial punctate keratopathy.

For these and other reasons including teratogenicity of IdUrd which has been demonstrated in newborn rats following systemic administration and in pregnant rabbits receiving the drug topically to the eye in doses similar to those used clinically in humans, efforts have been made to find replacement therapeutics.

One advantage of AIC has been established by the treatment of rabbits. In this study, experimental herpes simplex keratitis was established bilaterally in 16 rabbits. These were divided into 2 matched groups of 8. Each group was treated in a double blind fashion with topical drops at 4 hour intervals for 72 hours starting 24 hours after infection. The solutions administered were:
1. Saline (control)
2. AIC, 4 mg/ml Each eye was examined daily for 11 days and graded by two ophthalmologists. AIC at 4 mg/ml was effective therapeutically.

What is claimed is:
1. A compound selected from the group consisting of 5-iodo-5'-amino-2',5'-dideoxycytidine and the pharmaceutically acceptable acid addition salts thereof.
2. 5-Iodo-5'-amino-2',5'-dideoxycytidine.
3. 5-Iodo-5'-O-p-tolylsulfonyl-2'-deoxycytidine.
4. 5-Iodo-5'-azido-2',5'-dideoxycytidine.
5. A pharmaceutical composition containing an effective amount of a compound for treating herpes simplex virus infection in mammals, said compound being selected from the group consisting of 5-iodo-5'-amino-2',5'-dideoxycytidine and the pharmaceutically acceptable acid addition salts thereof together with a pharmaceutically acceptable carrier.
6. A composition of claim 5 containing 5-iodo-5'-amino-2',5'-dideoxycytidine.
7. A method of treating a herpes simplex virus infection in a host mammal afflicted with such infection which comprises administering to the said host an amount of a compound which is effective for treating a herpes simplex virus infection, said compound being selected from the group consisting of 5-iodo-5'-amino-2',5'-dideoxycytidine and the pharmaceutically acceptable acid salts thereof.

* * * * *